United States Patent [19]

Gersten et al.

[11] Patent Number: 5,018,850

[45] Date of Patent: May 28, 1991

[54] ILLUMINATED RING DEVICE

[75] Inventors: Martin Gersten; Roy Maus, both of Brooklyn; Lars Tibbling, New York, all of N.Y.

[73] Assignee: Computed Anatomy Incorporated, New York, N.Y.

[21] Appl. No.: 492,939

[22] Filed: Mar. 13, 1990

[51] Int. Cl.$^5$ .............................................. A61B 3/10
[52] U.S. Cl. .................................................. 351/212
[58] Field of Search ................... 351/212, 221; 362/32

[56]  References Cited

U.S. PATENT DOCUMENTS 3,932,030  1/1976  Hasegawa et al. .................. 351/212

4,772,115  9/1988  Gersten et al. ...................... 351/212

Primary Examiner—Paul M. Dzierzynski

[57] ABSTRACT

A cylindrical keratoscope is provided with an improved structure for illuminating the rings disposed along the length of its bore by having the light-transmitting rings defined as the lands between a series of opaquely coated, incised circular grooves in the bore. A circular, fluorescent, light tube is disposed in an aluminum light box having a semi-toroidal concavity provided with a light-reflecting surface to direct or collimate the light from the tube toward the light-receiving base of the device.

5 Claims, 1 Drawing Sheet

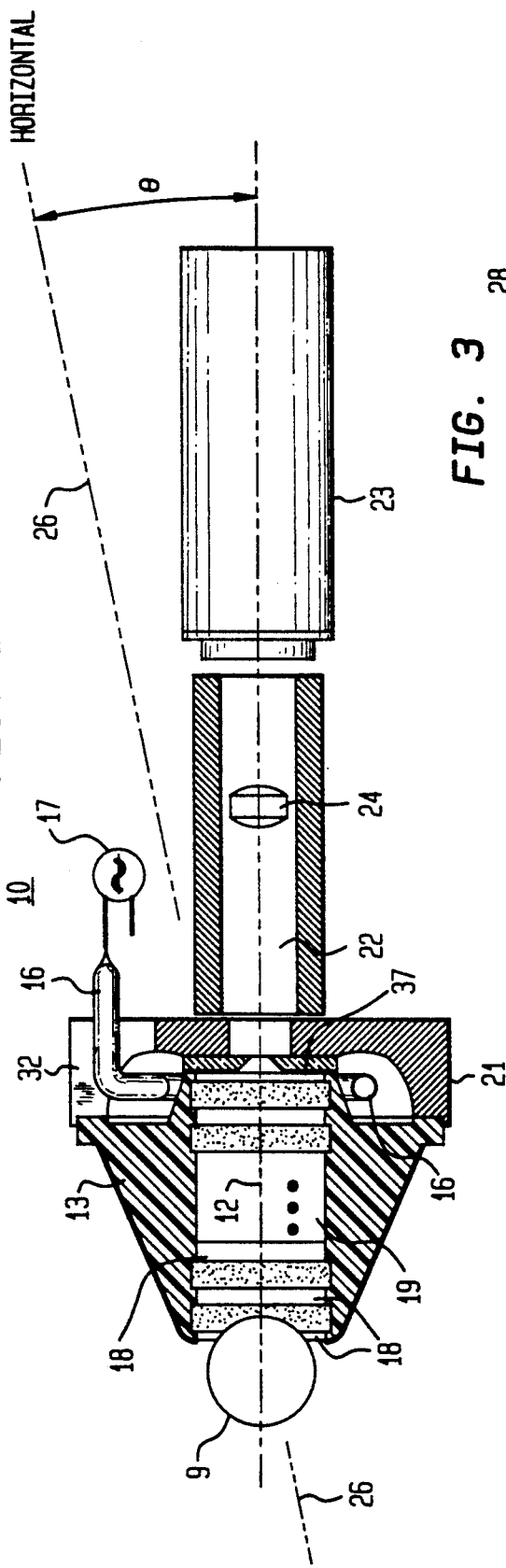
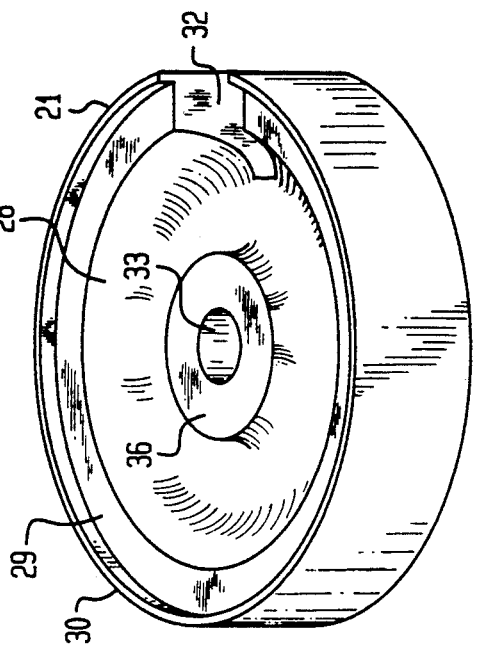
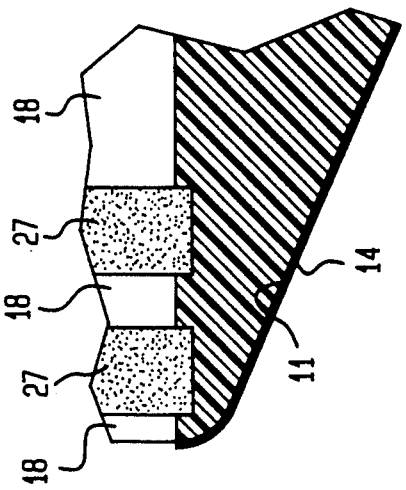
FIG. 1
FIG. 2
FIG. 3

ILLUMINATED RING DEVICE

TECHNICAL FIELD

This invention relates to illuminated ring devices for examining the topography of curved reflective surfaces and, more particularly, to keratoscopes and other corneal measuring instruments.

BACKGROUND ART

Among the known illuminated ring devices employed in observing the topography of the corneal surface must be included the original 1880 disc of Placido and the keratometer of Kilmer disclosed in U.S. Pat. No. 3,797,921 both of which used rather large hemispherical targets as well as the device of Knoll U.S. Pat. No. 3,248,162 which used a comparatively large diameter cylindrical target. An alternative to these large target devices is disclosed in U.S. Pat. No. 4,772,115 to Martin Gersten, Richard J. Mammone, and Joseph Zelvin. That device included a conical structure of translucent plastic having an opaquely coated hollow axial bore or passage whose diameter was only slightly larger than that of the object, typically the cornea of a patient's eye which was to be positioned adjacent to the bore at the cone's apical end. The opaque coating of the cylindrical bore was incised with a plurality of ring-shaped cuts to allow light which entered from a light box at the cone's base to illuminate the incised rings. An observer, or properly focused camera, looking into the bore's opposite end could acquire an image of the ring pattern appearing on, i.e., reflected from, the object. Variations in the radius of the rings in the pattern from circularity represent distortions of the curved surface.

While the aforementioned conical device has achieved a certain measure of success, the array of incandescent lamps in the lightbox which was required to provide sufficient illumination of the rings generated a considerable amount of heat. Also, the controlling the thickness of the opaque coating and the incising of the coating in the bore to define the light transmitting rings have proven to be difficult operations to control precisely; sometimes the coating would chip or be scratched off during processing or in the course of use. As a result, some rings were not precisely formed, and their images as reflected from the corneal surface were indistinct.

DISCLOSURE OF INVENTION

The burden of the foregoing difficulties is eased in accordance with the present invention by providing an improved light box structure from which the array of incandescent lamps has entirely been eliminated thereby obviating the heat generation problem. Instead, a ring-shaped gaseous discharge source, such as a fluorescent light tube, is disposed adjacent to the base of the cone. The light box is advantageously fabricated of aluminum and its rear wall is provided a with a semi-toroidal, reflectively coated concavity whose median diameter is substantially equal to that of the fluorescent lamp. The fluorescent lamp is positioned in the concavity so as to achieve a sort of collimation or direction of the lamplight toward the base of the cone. This gives a level of illumination, comparable to that achieved with incandescent lamps, but without the heat generation problems.

In the illustrative embodiment, the light transmitting rings are not incised into the coated bore. Instead, prior to the coating of the bore, the bore is first incised with a series of rings which will not, however, be the light-transmitting rings when the device is put to use. Instead, after the rings are incised, the bore is provided with an opaque coating which fills the incised rings. The bore is then bored or machined to form uncoated lands by removing the coating between the rings. The bottom and the side walls of the incised rings, however, continue to retain the opaque coating. Accordingly, in the new embodiment, light entering the base of the cone from the lightbox is transmitted to the bore of the device through the lands between the opaquely coated incised rings.

BRIEF DESCRIPTION OF DRAWINGS

FIG. 1 shows a cross-sectional view of one embodiment of the apparatus of our invention;

FIG. 2 illustrates a partial cross-sectional view of a portion of one embodiment of the apparatus of FIG. 1; and FIG. 3 is a front side perspective of the rear wall of the light box used in the embodiment of FIG. 1.

BEST MODE FOR CARRYING OUT THE INVENTION

In FIG. 1 there is shown in schematic form, and partly in central cross section taken along an optical axis, several elements of an instrument 10, such as a keratoscope, for producing a series of illuminated rings or mires to appear on the surface of an object whose contours are to be studied. The mounting of instrument 10 is advantageously made adjustable by any suitable means (not shown) so that its optical axis 12 may lie at a convenient "down angle" of approximately 10 degrees below the horizontal, indicated schematically by a line 26. The down angle accommodates the varying cranial overhang of different patients' eye sockets.

The present illustrative embodiment 10 employs a cone 13 of translucent plastic material having a central, cylindrical bore 19 defining the longitudinal axis 12 of the device. The bore is lined by a set of illuminated spaced, translucent rings 18. The 9, whose contours are to be observed, is placed adjacent to the bore 19 at the apical end of the cone. Light from the light box 21 mounted at the base end of the cone illuminates translucent rings 18 spaced along the interior of a cylindrical bore 19. A reflection of rings 18 appears behind the surface of the object 9 and will appear as concentric circles but only if the surface is truly spherical.

The image so appearing on object 9 may be acquired by an observation means such as a camera system including an extension tube 22, a camera 23, and a lens 24, also coaxial with the visual axis 12. The camera is advantageously coupled to a computer controlled data collection, analysis, and display system not shown nor necessary for an understanding of the present invention. Such computer controlled systems are known in the art as indicated in the aforementioned Gersten et al. patent.

The improved light box 21 of the present invention is provided with a semi-toroidal concavity 28 for collimating or directing the light of the circular fluorescent tube 16 toward the base of the cone 13. Light from fluorescent tube 16, energized from electrical power source 17, enters the uncoated base of the translucent plastic cone 13 flooding the interior of cone 13 with light. To enhance the reflection of light from within cone 13 out through translucent rings 18, the exterior conical surface of is advantageously provided with a coat of white reflective paint 11. When the white reflective coating has dried an opaque protective coating 14 of any color, typically black, may be applied on the outside.

The improved light-transmitting rings of the illustrative embodiment of FIG. 1 are achieved by first incising the series of annular rings in bore 19 and then coating the bore with an opaque material, preferably black in color. The bore is then enlarged to a depth less than that of the incised rings to remove the coating and reveal a series of uncoated lands between the incised rings, the side walls and floors of which retain the opaque coating.

Cone 13 may also advantageously be provided with a chamfered, uncoated external extension portion 13' adjacent to the last translucent ring 18' at the base end of cone 13 so that ring 18' will receive its light directly from lamp 16 rather than by reflection through the base.

As mentioned above, the prior art illuminated ring device had its transparent rings formed by cutting through the opaque coating of the bore to expose the translucent plastic. In a passage 19 that may be five to eight centimeters in length and have about a three centimeter diameter, with 20 or 30 transparent rings along its interior, it can be appreciated that small variations in the thickness of the passage coating or in the regularity of the edge of a coated region defining a transparent ring can have a significant effect on the distinctness of the rings appearing on the surface of object 9.

An additional refinement is present in FIG. 1 in that fluorescent tube 16 and camera 23 may advantageously be chosen so that the phosphor employed in tube 16 is properly coordinated with the spectral response of the chip employed in camera 23. Matching the spectral responses provides better sensitivity of camera focus. However, it is important in a corneal measuring device that focus be achieved within the visible light spectrum. For example, where camera 23 employs a CCD chip, its spectral response may be found to be peaked toward the infra-red end of the light spectrum. Since it is undesirable to base corneal image measurements on infra-red response, the use of a fluorescent phosphor in tube 16 which produces no infra-red output is highly desirable. In addition, the color of the phosphor may advantageously be specified as green because the reflectivity of the human iris is lower for green so that the corneal image will have a "blacker" background between the illuminated·rings due to the reduced amount of reflection than would occur with a white phosphor.

FIG. 2 illustrates a portion of the tip of cone 13 near eye 11, and it is shown enlarged to illustrate better the technique employed. After bore 19 has been formed in cone 13, grooves are machined into the transparent material of the bore at the respective positions where there are to be opaque rings. The machined depth of the grooves is advantageously about 0.16 millimeter, but that depth is not critical. The number, spacing, and width along passage 19 of the grooves are chosen according to the particular application contemplated, e.g. the type of corneal malady to be measured or the type of surface to be examined. However, for convenience of illustration only a few equal opaque and transparent rings are shown. After the grooves have been formed, the entire interior of the passage 19, including both sidewalls and the bottom of each groove, is coated with opaque material; and then the coating is machined away to expose the ungrooved rings 18, i.e. the lands, between adjacent now-opaque grooves 27. Opaque coating in the grooves remains undisturbed. Since the passage 19 diameter can be easily controlled during initial manufacture and during the coating removal process, the exact thickness of the coating within the grooves is immaterial insofar as precise and consistent definition of transparent rings is concerned.

Further in accordance with the principles of the improved embodiment, light box 21 is advantageously fabricated of a cylindrical block of aluminum having a semi-toroidal concavity 28 whose surface is highly polished to be reflective. The median diameter of concavity 28 approximates that of fluorescent lamp 16. An opening 32 in light box 21 accommodates ends of the circular fluorescent tube 16 which are electrically connected to supply 17.

The central portion of light box 21 is provided with an opening 33 that is coaxial with visual axis 12 and a recessed circular seat 36 which accommodates disk 20. Disk 20 is a toroid of trapezoidal cross section with its interior edge beveled to face the eye 11. An outer diameter of the disk is approximately the same as that of the seat 36, and an inner diameter is sufficient to pass focused light of the reflected image from eye 11. The disk 20 is also formed of transparent plastic material and is inserted between director 13 and reflector 21 to provide at least one additional illuminated ring 36. To that end, an opaque coating is applied to at least the left face (as illustrated). The coating is removed from an portion of the left face of disk 20 in the shape of an annular ring 37 that is concentric with inner and outer edges of the disk. Light from fluorescent tube 16 enters the outer edge of disk 20 to illuminate the ring 37 by back lighting.

As can be seen in the drawing, semi-toroidal concavity 28 is approximately circular in cross section; and the circular portion of toroidal tube 16 is advantageously located with its toroidal loop center line approximately coincident with a circle including the centers for arcs of circles comprising that circular cross section. Thus, substantially all of the light emitted from tube 16 is directed toward the base of cone 13. Although concavity has been illustrated as being of semi-circular cross section, it is expected that somewhat greater intensification of illumination may be achieved by use of a parabolic cross section and by locating 16 so that it is at the foci of the parabolic cross section.

Although the invention has been illustrated in terms of one particular embodiment, modifications which will be apparent to those skilled in the art are included within the spirit and scope of the invention.

What is claimed is:

1. Apparatus for providing an illuminated pattern on an object comprising:
    a conically shaped body of light previous material having a cylindrical bore defining a series of successive opaque and light transmitting rings and a substantially circular base portion for receiving the light to be transmitted through said rings, said opaque rings being incised in said bore and filled with an opaque coating,
    a toroidal, light-emitting device, and
    a light box of structurally rigid material for mounting said base portion of said conically shaped body, said light box having a semi-toroidal concavity for accommodating said light emitting device and maintaining said device substantially at the focus of said concavity, thereby to cause substantially all of the light from said device to be transmitted toward said base portion of said conically shaped body.

2. Apparatus according to claim 1 wherein said light emitting device is a fluorescent lamp.

3. Apparatus according to claim 2 wherein said light box for mounting said light-emitting device is an aluminum housing and said semi-toroidal concavity is approximately semi-circular in cross-section and is provided with a specular reflective surface.

4. Apparatus according to claim 2 further comprising a camera for acquiring an image of said pattern and wherein the light spectrum output of said fluorescent lamp is coordinated with the spectral response of said camera, thereby to improve the sharpness of said image acquired by said camera.

5. Apparatus according to claim 2 wherein the color of light emitted by said fluorescent lamp is coordinated with the color of said object to minimize certain reflections therefrom.

* * * * *